United States Patent
Durham

(10) Patent No.: US 9,931,884 B2
(45) Date of Patent: Apr. 3, 2018

(54) MARKER FOR OPTICAL MARK RESPONSE FORMS

(71) Applicant: Amara Rahman Durham, Dallas, TX (US)

(72) Inventor: Amara Rahman Durham, Dallas, TX (US)

(73) Assignee: Amara Rahman Durham, Dallas, TX (US)

( * ) Notice: Subject to any disclaimer, the term of this patent is extended or adjusted under 35 U.S.C. 154(b) by 0 days.

(21) Appl. No.: 15/294,715

(22) Filed: Oct. 15, 2016

(65) Prior Publication Data

US 2017/0028770 A1    Feb. 2, 2017

Related U.S. Application Data

(60) Division of application No. 14/245,808, filed on Apr. 14, 2014, now Pat. No. 9,470,628, which is a
(Continued)

(51) Int. Cl.

| B43K 27/04 | (2006.01) |
|---|---|
| B43K 27/08 | (2006.01) |
| B43K 1/12 | (2006.01) |
| B43K 8/00 | (2006.01) |
| B43K 8/02 | (2006.01) |
| B43K 8/03 | (2006.01) |
| B43K 8/06 | (2006.01) |
| B43K 8/08 | (2006.01) |
| B43K 27/02 | (2006.01) |
| B43K 29/05 | (2006.01) |
| B43L 19/00 | (2006.01) |
| G09B 3/00 | (2006.01) |

(Continued)

(52) U.S. Cl.
CPC ............... *B43K 27/08* (2013.01); *B43K 1/12* (2013.01); *B43K 8/003* (2013.01); *B43K 8/022* (2013.01); *B43K 8/03* (2013.01); *B43K 8/06* (2013.01); *B43K 8/08* (2013.01); *B43K 27/02* (2013.01); *B43K 29/05* (2013.01); *B43L 19/0018* (2013.01); *B43L 19/0068* (2013.01); *G01N 21/55* (2013.01); *G09B 3/00* (2013.01); *G09B 19/00* (2013.01)

(58) Field of Classification Search
CPC . B43K 8/022; B43K 8/03; B43K 8/06; B43K 27/02; B43K 27/04; B43K 27/08; B43K 27/12
USPC ........................................................ 401/17, 35
See application file for complete search history.

(56) References Cited

U.S. PATENT DOCUMENTS

| 3,887,287 A | 6/1975 | Rosh, Jr. |
|---|---|---|
| 5,213,373 A | 5/1993 | Ramos |

(Continued)

*Primary Examiner* — Jennifer C Chiang
(74) *Attorney, Agent, or Firm* — Slater Matsil, LLP

(57) ABSTRACT

A writing instrument includes a first reservoir for dispensing a first fluid having a first property of reflectivity. A first tip member is in fluid connection with the first reservoir. The first tip member has an end with a size and shape that corresponds to a response area of the response form. A second reservoir can be used for dispensing a second fluid, which is capable of modifying the first property of reflectivity when covering the first fluid. A second tip member is in fluid connection with the second reservoir. The second tip member has an end with a size and shape that corresponds to the response area of the response form.

20 Claims, 5 Drawing Sheets

Related U.S. Application Data continuation of application No. 11/771,940, filed on Jun. 29, 2007, now Pat. No. 8,690,464.

(51) Int. Cl.
  *G09B 19/00*   (2006.01)
  *G01N 21/55*   (2014.01)

(56) References Cited

U.S. PATENT DOCUMENTS

| | | | |
|---|---|---|---|
| 5,899,619 A * | 5/1999 | O'Shei | B43K 8/003 401/14 |
| 6,004,057 A * | 12/1999 | Fulop | B43K 27/08 401/17 |
| 6,179,501 B1 * | 1/2001 | Fulop | B43K 27/08 401/17 |
| 6,213,664 B1 | 4/2001 | Kondo | |
| 6,357,943 B1 | 3/2002 | Kuang | |
| 6,921,223 B2 | 7/2005 | Marschand | |
| 7,001,091 B1 | 2/2006 | Knight | |
| 7,018,122 B2 | 3/2006 | Kwan et al. | |
| 7,070,115 B2 | 7/2006 | DeBaise | |
| 7,070,352 B2 | 7/2006 | Iida et al. | |
| 7,083,352 B2 | 8/2006 | Ando et al. | |
| 8,011,845 B2 | 9/2011 | Ho | |

* cited by examiner

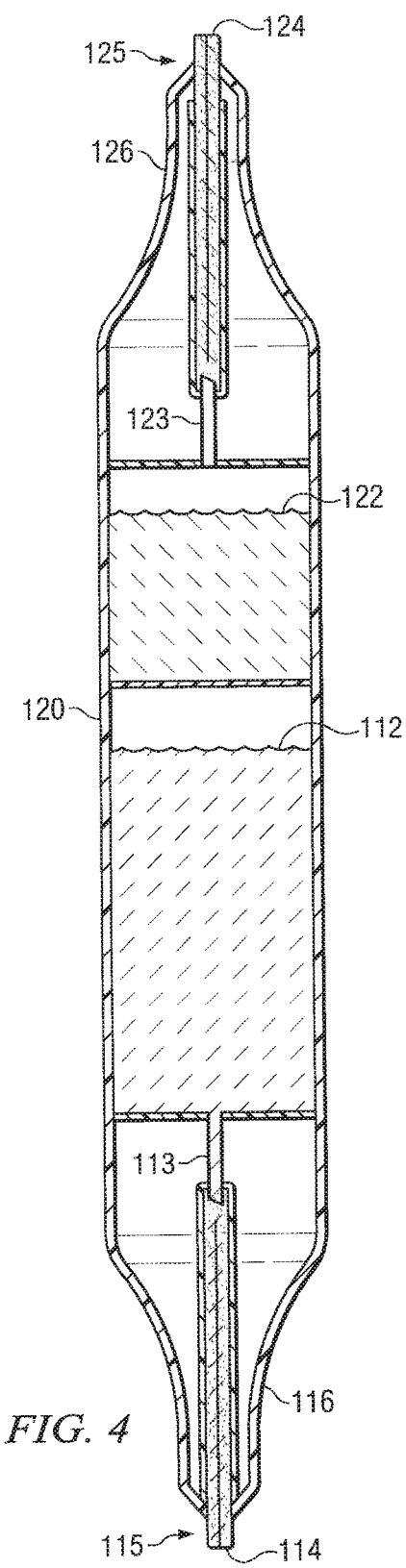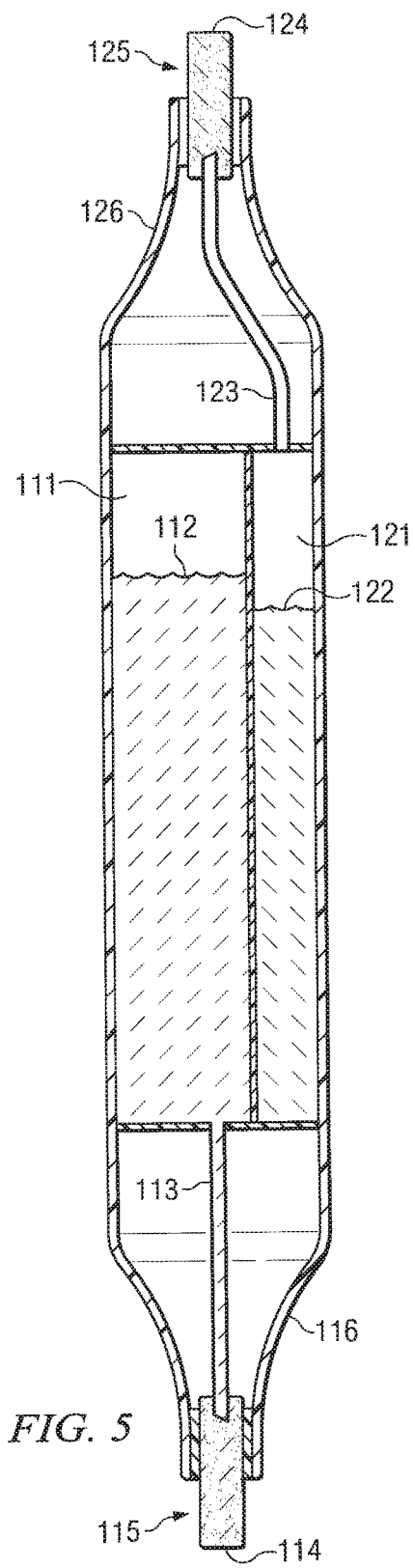
FIG. 4
FIG. 5

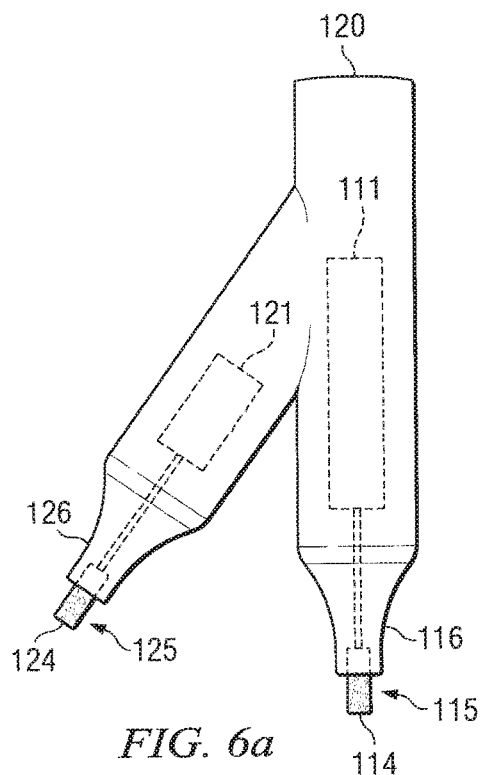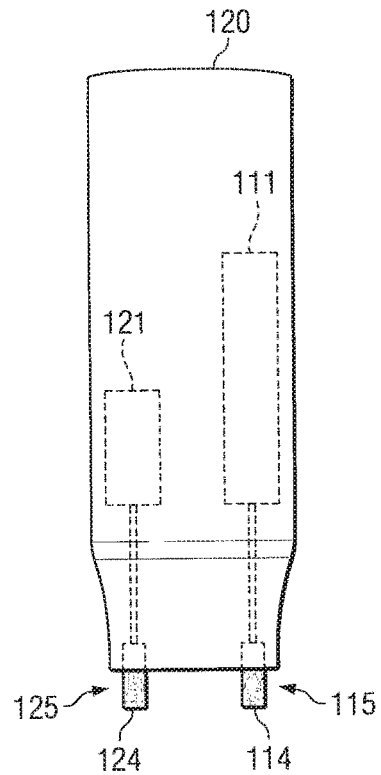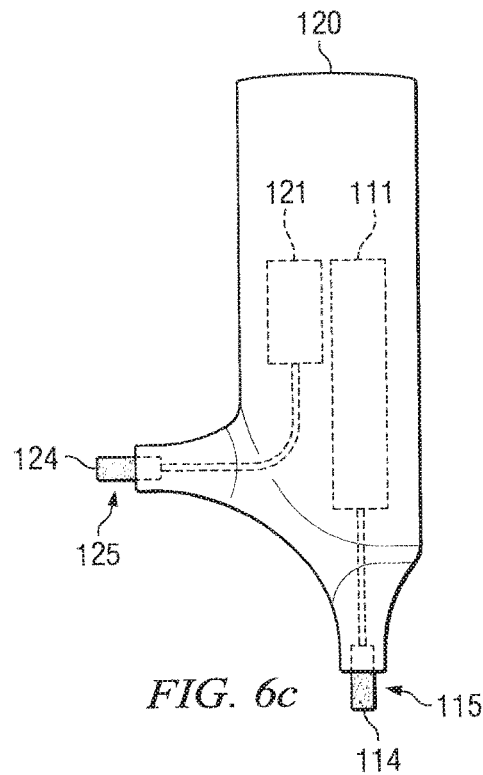
FIG. 6a
FIG. 6b
FIG. 6c

MARKER FOR OPTICAL MARK RESPONSE FORMS

CROSS-REFERENCE TO RELATED APPLICATIONS

This application is a divisional of U.S. patent application Ser. No. 14/245,808, filed Apr. 4, 2014 (now U.S. Pat. No. 9,470,628), which is a continuation of U.S. patent application Ser. No. 11/771,940, filed Jun. 29, 2007 (now U.S. Pat. No. 8,690,464), which application is hereby incorporated herein by reference.

TECHNICAL FIELD

One embodiment of this invention relates to writing instruments, and more particularly to a marker for optical mark response forms.

BACKGROUND

Optical Mark Response (OMR) forms are used for such things as standardized tests, games or contests, such as the lottery or keno, surveys, and digital database entry. Some examples of digital database entry forms include government forms, such as used in voting, as well as forms used by the medical and insurance industries for data collection. OMR machines are calibrated to read responses on OMR forms as positive responses if marks are non-reflective and negative if marks are reflective. The benefits of OMR scanning is the speed over manual data entry, the accuracy from eliminating potential human error, and the cost savings resulting from reducing administrative staff and reducing the time needed to collect data in the business cycle.

Currently, number two pencils are the standard writing instruments on OMR response forms. An OMR reader relies upon the reflective and non-reflective nature of the written trace. For example, an OMR reader may rely on the fact that the paper is reflective for incident light while the lead from the pencil is non-reflective. In this manner, the reader can distinguish the place where the paper has been marked.

Besides pencils, other writing instruments are known in the art. For example, U.S. Pat. No. 7,018,122 discloses a writing instrument that includes a tubular, ink-impermeable body portion containing a plurality of reservoirs that are housed adjacent to each other, wherein each reservoir is separated from an adjacent reservoir by a reservoir barrier. A multi-sectioned nib is disposed at one end of the writing instrument. The nib includes a plurality of nib sections disposed adjacent to each other and separated from an adjacent nib section by a nib section barrier at a writing end, such that the nib sections do not communicate materials contained therein between adjacent nib sections. The opposite ends of the nib section are spaced from each other and disposed within the tubular body portion such that each nib section is disposed in communication with a different reservoir.

U.S. Pat. No. 7,083,352 discloses a ballpoint pen including a tip body made of metal having a front edge part and a plurality of inward protrusions. A ball is rotatably embraced between the front edge part and the inward protrusions. A rod part urges the ball forwardly and brings the ball into close contact with the inner surface of the front edge part. Ink outflow gaps are formed each between the adjacent inward protrusions.

U.S. Pat. No. 7,070,352 discloses a writing implement that includes a cylindrical shaft member. A pen tip member is fixed to one end of the shaft member. Colored ink seeps out of the pen tip member. Liquid, such as ink, is stored in the shaft member.

U.S. Pat. No. 7,001,091 discloses a pen that includes a housing. A first reservoir inside the housing is configured to contain a first fluid. The first reservoir includes a first opening configured to dispense the first fluid. A second reservoir inside the housing is configured to contain a second fluid. The second reservoir includes a second opening configured to dispense the second fluid. A first writing tip extending from the housing is configured to dispense a substantially homogeneously mixed fluid to a writing surface.

U.S. Pat. No. 3,887,287 describes a multi-color marking implement having a number of flat-faced, adjacent marking nibs communicating with a plurality of nib-wicks, containing inks of different colors.

SUMMARY

In one aspect, the present invention provides a writing instrument that can enhance the speed and accuracy for a respondent using an OMR form. In various examples, this writing instrument can be used for test taking, lottery, keno, surveys, and any other information-gathering items such as in digital database entry. Some examples of digital data entry forms include, government forms, such as in voting, as well as other data entry as used in the medical and insurance industries.

In a further aspect, the writing instrument's trace changes the reflective and non-reflective nature of the selected response areas of the response form. Hence the instrument changes the reading from an OMR reader that relies on optical reflectivity of the paper. Preferably, the tip of the writing instrument has a shape that corresponds to the answer areas (e.g., "bubbles") of the form.

An aspect of the writing instrument is its ability to write or mark with fluids of multiple optical reflectivities. In a particular embodiment, the writing instrument writes or marks with fluids having two different optical reflectivities. This is accomplished by the inclusion of two independent, optically (e.g., reflectively) different fluids. The two fluids are contained in their respective reservoirs and flow out via different tips without mixing. For example, the application of a coating of the second fluid on a surface coated with the first fluid results in an increased optical reflectance of the surface. In particular, when optically scanned, this increased optical reflectivity translates to a machine reading the form, opposite to that obtained after the application of the first fluid marker. Both fluids are quick drying to enable fast application of overcoats (and still referred to as fluids in their dried state). Accordingly, the use of this pen results in increased speed and accuracy for a respondent using an OMR form.

One use of embodiments of the current invention involves a method of conducting a test by providing test questions to a plurality of test takers. The test takers are provided answer sheets having a plurality of answer areas. In this embodiment, at least some of the answer sheets contain answers marked with both reflecting and non-reflecting fluids. The answer sheets are subsequently evaluated using an optical reading apparatus.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 1, which includes

FIG. 4 is an alternate embodiment of the present invention using a different tip member design;

FIG. 5 is another alternate embodiment of the present invention with a different reservoir design;

FIGS. 6a-6c are alternate embodiments of the present invention, whereby the two tip ends are placed at different locations on the writing instrument.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, namely a writing instrument for optical marker response forms. The invention may also be applied, however, to other applications that require machine scanning of data. Similarly, although the present invention relates to the modulation of optical property of a surface (such as a response form) for an optical sensor, the invention can also be applied to other types of sensors.

One use of aspects of the present invention will be described with respect to a specific embodiment, namely optical mark response forms used in a testing environment. In one aspect, the present invention provides a writing instrument where the writing tip is formed in a shape that matches a corresponding optical mark response form. As will be discussed further below, the invention can also be used in a wide variety of other contexts.

Standardized tests are designed in such a way that the questions, the conditions for administering scoring procedures, and the interpretations are consistent and are administered and scored in a predetermined, standard manner. "Standardized" tests use the same standards to measure student performance across a region such as a school, school district, state, or country as examples. Everyone takes the same test according to the same rules. This scheme makes it possible to measure each student's performance against that of others.

In one embodiment, the present invention provides a writing instrument that can be used with a standardized (or non-standardized) test, or for that matter, any other OMR form. As will be described in the preferred embodiment, the writing instrument is capable of using two types of fluids (such as ink). Conceptually, these two fluids can be used to "mark" or "erase" the previously marked response portions of the forms.

Figure 1B:
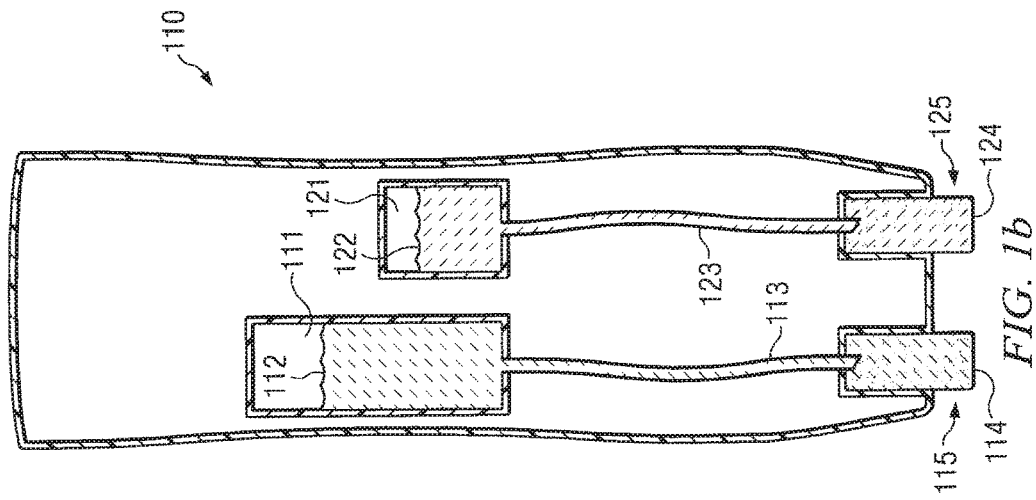
FIGS. 1a and 1b, illustrates an embodiment of present invention.
Figure 1A:
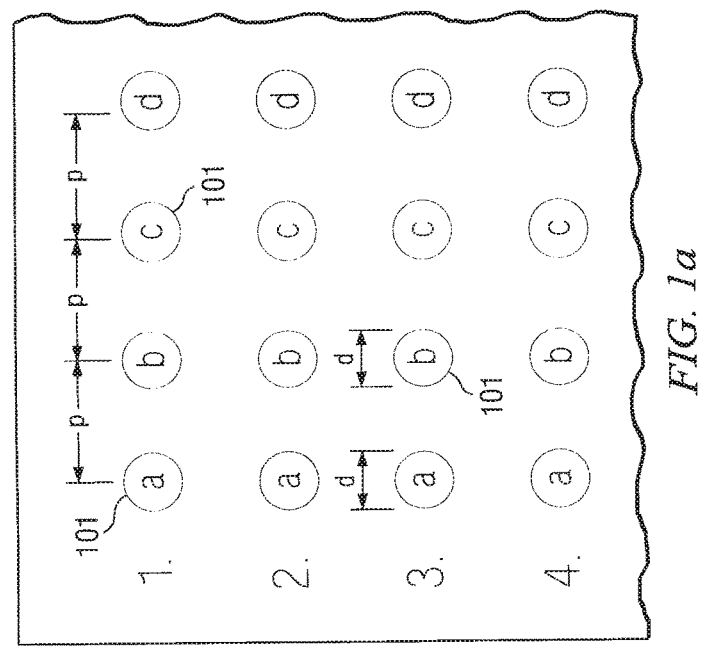
Figure 2A:
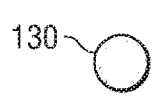
FIGS. 2a-2g illustrate the possible shapes of response areas and or a cross-sectional view of the tip ends of the writing instrument.
Figure 2B:
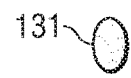
Figure 2C:
Figure 2D:
Figure 2E:
Figure 2F:
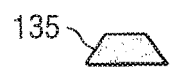
Figure 2G:
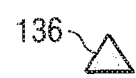

FIGS. 1a and 1b illustrate the functional embodiment of the present invention. FIG. 1a shows an OMR form 100. The OMR form 100 contains a plurality of response areas 101. Each response area 101 of the form has an associated shape and area. FIG. 1a also illustrates the maximum diameter (d) of the response area 101 and the distance (p) between the center points of the response areas.

The OMR reader measures the optical reflectivity of this response area 101 to determine the user response.

FIG. 1b illustrates the functional relationships of the elements encased in the writing instrument 110. As will be discussed below, the physical configuration can take on many forms. A first reservoir in for the first fluid 112 is functionally connected to the first tip member 115 of the writing instrument 100. This connection is made via the connecting tube 113, which can serve to regulate the amount of fluid reaching the first tip member 115. This first fluid 112 can be applied or coated onto a surface of a response form using the first tip member end 114. A calibrated OMR machine conclusively identifies the portion of the surface on the response form that has been coated.

Similarly, a second reservoir 121 for the second fluid 122 is functionally connected to the second tip member 125 via the connecting tube 123. The two liquids are chosen to have different optical reflectivities when dried upon a response form 100. The second fluid 122, if applied on to a response form 100 already marked with the first fluid 112, modifies the optical reflectivity of the response area. Subsequently, the calibrated OMR machine again conclusively identifies the surface of the response form 100 coated with second fluid 122 applied on to a response form 100 already marked with the first fluid 112. However, the identified response of the OMR machine is opposite to the response of an area marked by the first fluid 112.

In one specific example, the first fluid 112 has an optical reflectivity such that it is non-reflective when applied to the response area 101 of the form 100. However, the second fluid 122 increases the reflectivity of the response area 101 when applied over a surface coated with the first fluid 112. In some cases, the second fluid 122 may decrease the reflectivity of the response area 101 when applied over the first fluid 112.

The physical properties of the fluids (such as viscosity, specific gravity, and acidity) are selected to work with the given flow system. The optical property of the fluids 112 and 122 may be obtained by the addition of an appropriate colorant to a suitable solvent. The solvent in the fluids 112 and 122 could be either water, oil, alcohol or any suitable liquid. Besides the colorant, the fluids 112 and 122 may also contain other additives such as resins, surface tension modifiers, viscosity modifiers, pH modifiers, humectants, biocides, or other suitable additives. An example of the first fluid 112 is a black ink. IJ BK 68 produced by OCP GmbH is one specific example of the first black fluid. IJ BK 68 consists of water (75-80%), glycerin (approximately 5%), solvents (0.5-2%), alcoholic mixtures (5-8%), water soluble dyes, modifiers, and auxiliaries (tensides). An example of the second fluid 122 is a white ink. This white ink is preferably intense enough to cover the first fluid 112 while drying quickly enough to write over again with the non-reflective liquid. As an alternative, a correction fluid, such as used with Wite-Out™ or Liquid Paper™, could be used.

The size and shape of the reservoir can be matched to maximize user performance and usage. For example, if more use of the first fluid 112 is anticipated than the second fluid 122 (as it would be in most cases), the volume of the first reservoir 111 can be made larger relative to the second reservoir 121. Similarly, the shapes of the reservoirs 111 and 121 and the housing 120 in FIG. 3 can be adapted for performance and comfort and/or style. Hence, they may be cubical, spherical, cylindrical, pyramidal, or any suitable shape.

The size and shape of the ends of both the first tip member end 114 and second tip member end 124 preferably correspond to the associated shape and area of the response area 101 of the OMR form 100. In general, these shapes can be any closed shape. Several examples are illustrated FIGS. 2a-2g. In these figures, the ends of the tip members could be a circle 130, an oval 131, a square 132, a diamond 133, a rectangle 134, a trapezoid 135, a triangle 136, or any other preferred shape. In the specific example of FIG. 1b, the tip member ends 114 and 124 and the associated response area 101 corresponds to a circle 130. In some embodiments, the shape of the second tip member 125 may be different from the first tip member 115. For example the second tip member end 124 may be an oblong or oval shaped whereas, the first tip member end 114 may be circular.

The size of the first and second tip member ends 114 and 124 in relation to the size of the response area 101 is described referring to FIG. 1a. In preferred embodiments, the first tip member end 114 is larger than the size of the response surface area lot In the preferred embodiment, the maximum diameter (W) of the first tip member end 114 varies from about the maximum diameter (d) of the response area 101 to about the distance between the response areas (p) or d<W<p. Typically, the maximum diameter W of the first tip member end 114 is about half the sum of the maximum diameter (d) and distance between the response area (p) or W=(d+p)/2. In some embodiments, the first tip member end 114 may be about 1% to 10% larger than the size of the response surface area 101.

The second tip member end 124 may be larger than the first tip member end 114 to enable faster erase times. Preferably, the maximum diameter (E) of the second tip member end 124 varies from about the maximum diameter (d) of the response area 101 to about the distance given by the expression 2p-d or in other words d<E<2p-d. Preferably, the maximum diameter E of the second tip member end 124 is about the distance between the response area (p) or E=p.

If the distance p between the center points of response areas 101 on the form 100 is not symmetric, i.e., adjacent response areas 101 in the horizontal direction are separated a first distance $p_x$ and adjacent response areas in the vertical direction are separated by a second distance $p_y$, the expressions for the first tip member end 114 and the second tip member end 124 may be suitably modified. For example, the maximum diameter E of the second tip member end 124 in such an embodiment would preferably follow the expressions d<E<2$p_x$-d and E<2$p_y$-d.

In different embodiments, the second tip member end 124 may be about 1% to 10% larger than the first tip member end 114. In a particular example, the second tip member end 124 is 10% larger than the first tip member end 114. Further, the ratio of the cross-sectional sizes of the tip ends 114 and 124 to the size of the response area 101 is selected to minimize the correction time. Hence, this ratio may be around 1.0 to 1.1. However, this ratio of the cross-sectional size of the tip ends 114 and 124 to the size of the response area 101 maybe also be between 0.9 to 1 and 1.1 to 1.

The second tip member end 124 may also be smaller than the first tip member end 114. This may be introduced, for instance to avoid accidental erasure of marked adjacent response areas. In such instances, for example, the second tip member end 124 may be about 1% to 10% smaller than the first tip member end 114.

A user applies this preferred embodiment, by using the first tip member end 114 to "mark" positive responses and the second tip member end 124 to "erase" previously marked responses.

In a preferred use of the invention, a test taker uses the writing instrument 110 to answer responses to a test whose answer sheet or response form has multiple response areas 101 as in form 100. The test taker fills the response area or answer area 101 with the writing instrument 110 The test taker uses the first tip member end 114 to record positive responses. If an undesired response is erroneously entered e.g., the test taker changes her mind, the test taker applies the second tip member end 124 and coats or applies a second layer using the second fluid 122 on the response area 101. This procedure can continue until the OMR form 100 is completed.

The completed response form 100 is then scanned using an OMR machine that only identifies the first fluid 112 layer as positive responses. The response areas coated with the second layer using the second fluid 122 do not record a positive response during the machine scan.

While described here with respect to test takers, it is understood that the concepts apply equally to other response forms used in places such as in games or contests (for example lottery or keno), digital database entry (for example, government forms such as in voting, as well as other data entry as in the medical and insurance industries and surveys).

In one aspect of using the current invention, at least one response form 100 (for example, answer sheet) in a test is marked with a reflective fluid but none of the answer areas 101 are marked with a non-reflective fluid. Similarly, some of the answer areas being marked with a reflective fluid may comprise answer areas marked with a reflective fluid that overlies a non-reflective fluid. In some cases, some test takers may use a normal pencil to mark the response. The provided answer sheet could either be a test form, a standardized test form, a lottery form, a game form, a survey form, a database entry form such as used in voting, gathering medical or insurance information, or any other optically scanned form.

Figure 3:
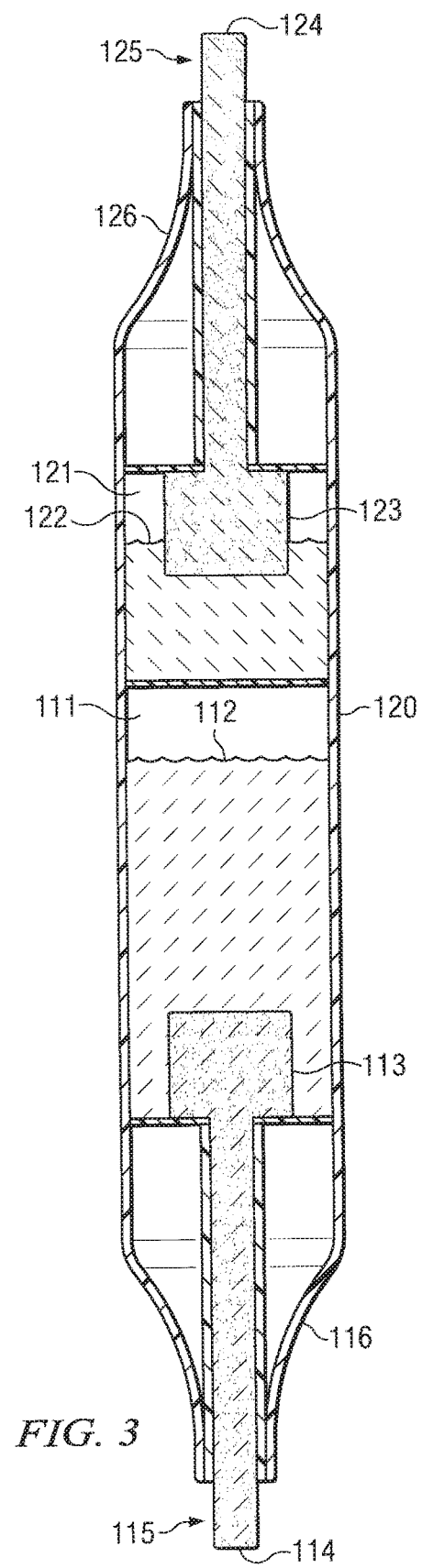
FIG. 3 is a preferred embodiment of present invention.

FIG. 3 illustrates a first exemplary embodiment of a writing instrument 120 that can use aspects of the invention. In this case, both the reservoirs 111 and 121 are located inside a housing 120, which may be made of a plastic or any other suitable material. In this specific example, the tip members 115 and 125 of the first and second members are located at opposite ends of the housing 120 and made of the same type of tip member. The tip members 115 and 125 are supported by ferrules 116 and 126. In the preferred embodiment, the fluid connectors 113 and 123 and the tip members 115 and 125 are made of a wick (such as a fibrous material) to regulate the flow of the fluid. The wick may be made of a fibrous material or any suitable material. Examples of the fibrous material include polyester, nylon, and polyolefin such as polypropylene or any other suitable polymeric material. In this preferred embodiment, the volume of the reservoir 121 is less than half, e.g., between about 20% to about 50%, of the volume of the reservoir 111. However, in some cases, this ratio could be suitably adjusted to user utilization and needs. Although in the preferred embodiment, only a part of the reservoirs 111 and 121 are filled with the wicking material, in some embodiments all of the reservoirs 111 and 121 may be filled with the wicking material.

FIG. 4 illustrates an alternative embodiment of the writing instrument 120 using a different tip member design. The tip members 115 and 125 in this example consist of nibs, while the fluid connectors 113 and 123 are made of small capillaries that regulate fluid flow. However, many variations in the tip member design are possible. In other embodiments of the present invention, the tip members 115 and 125 could also be a stamp, a roller ball, a wick, a felt tip end, a sponge, tape, or any other tip member. Accordingly, the various functional elements are modified to ensure a working writing instrument. The fluid connectors 113 and 123, reservoirs 111 and 121, and the fluids 112 and 122 would accordingly be modified to ensure a uniform and reliable fluid flow. A valve may be included as part of the fluid connectors 113 and 123 to regulate the flow of fluid through the tip members.

In the embodiments of FIGS. 3 and 4, the first and second tip members (115 and 125) are made of the same type of tip member. However, in alternate embodiments, the first and second tip members 115 and 125 may be made of different tip members. In a specific example, the first tip member 115 may be a nib whereas the second tip member 125 may be a wick.

In alternate embodiments, the locations of individual elements can be altered. In the embodiments of FIGS. 3 and 4, the reservoirs 111 and 121 were located in the respective upper and lower halves of the housing. The reservoirs 111 and 121 can however also be separated along the length of the writing instrument 120 as shown in FIG. 5.

In alternative embodiments shown in FIG. 6a-6c, the tip members 115 and 125 can also be located at an angle to each other (FIG. 6a), on the same side of the housing 120 (FIG. 6b), or perpendicular to each other (FIG. 6c). Various modifications to the locations of the tip members 115 and 125 and housing 120 are possible to improve comfort while maintaining speed and accuracy of the writing instrument.

Figure 7:
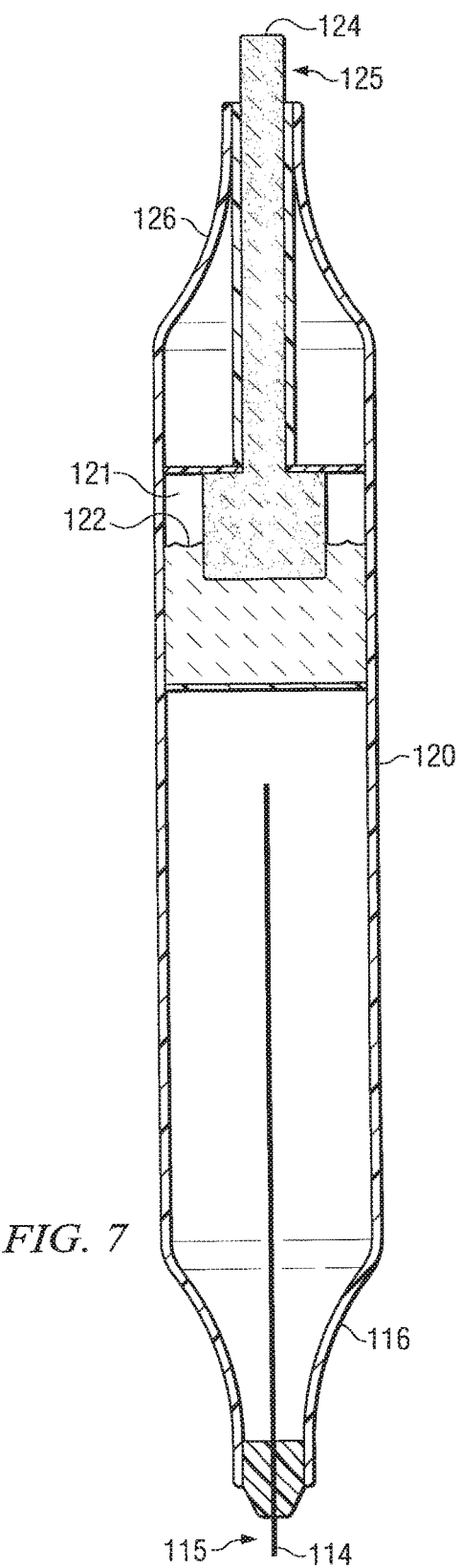
FIG. 7 is an alternate embodiment of the present invention using a different tip member design for the first and second tip member.

In yet another embodiment of the current invention, the first tip member 115 is a pencil and the second tip member 125 is a pen. FIG. 7 illustrates a specific example, where the first tip member 115 is a graphite pencil lead whereas the second tip member 125 is a marker pen. The test taker uses the mechanical pencil 115 to mark positive responses in an OMR form 100. The marker pen 125 with the second fluid 122 erases the responses marked by the mechanical pencil 115 on the OMR form 100.

Other modifications and variations are also possible. For example, the tips can be removable with their fluid chambers attached to the tip. In another example, the tips can be released from the housing by the push (or click) of a movable member.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A writing instrument to be used with a response form, the writing instrument comprising:
    a first reservoir for dispensing a first fluid having a first property of reflectivity;
    a first tip member in fluid connection with the first reservoir, the first tip member having an end with a size and shape that corresponds to a response area of the response form;
    a second reservoir for dispensing a second fluid, the second fluid capable of modifying the first property of reflectivity when covering the first fluid; and
    a second tip member in fluid connection with the second reservoir, the second tip member having an end with a size and shape that corresponds to the response area of the response form.

2. The writing instrument of claim 1, wherein the end of the second tip member is larger than the end of the first tip member.

3. The writing instrument of claim 1, wherein the first fluid is dispensed from the first reservoir to the first tip member by a wicking function.

4. The writing instrument of claim 1, wherein the first reservoir is at least twice the size of the second reservoir.

5. The writing instrument of claim 1, wherein the first tip member and the second tip member are a same type of tip member.

6. The writing instrument of claim 1, wherein the first tip member includes a stamp.

7. The writing instrument of claim 1, wherein the first tip member includes a nib.

8. The writing instrument of claim 1, wherein the first tip member includes a roller ball or a felt tip end.

9. The writing instrument of claim 1, wherein the second tip member includes a sponge.

10. The writing instrument of claim 1, further comprising a housing, wherein the first reservoir and the second reservoir are located in the housing, the first tip member being located at a first end of the housing and the second tip member being located an opposed second end of the housing.

11. The writing instrument of claim 1, wherein the end of the first tip member comprises a substantially circular-shaped end and the end of the second tip member comprises a substantially circular-shaped.

12. The writing instrument of claim 1, wherein the end of the first tip member comprises a substantially rectangular-shaped end and the end of the second tip member comprises a substantially rectangular-shaped end.

13. The writing instrument of claim 1, wherein the end of the first tip member comprises a substantially oval-shaped end and the end of the second tip member comprises a substantially oval-shaped end.

14. The writing instrument of claim 1, wherein the first property of reflectivity comprises a non-reflective property such that the first fluid is non-reflective when applied to the response area of the response form and the second fluid increases the first property of reflectivity of the response area when applied over the first fluid.

15. The writing instrument of claim 1 in combination with the response form.

16. The writing instrument of claim 15, wherein the end of the first tip member has a cross-sectional shape that is the same as a shape of the response area of the response form.

17. The writing instrument of claim 15, wherein the end of the first tip member has a cross-sectional size and the response form has the response area with a response size, wherein a ratio of the cross-sectional size to the response size is between 1 to 1 and 1.1 to 1.

18. The writing instrument of claim 15, wherein the response form comprises a form selected from the group consisting of a test form, a digital database entry form, a game form, a lottery form, a voting form, and a survey form.

19. A writing instrument comprising:
    a first reservoir for dispensing a first fluid having a first property of reflectivity;
    a first tip member in fluid connection with the first reservoir, the first tip member having an end with a size and shape that corresponds to response areas of a response form;
    a second reservoir for dispensing a second fluid, the second fluid capable of modifying the first property of reflectivity when covering the first fluid; and
    a second tip member in fluid connection with the second reservoir, the second tip member having an end with a size and shape that corresponds to the response areas of the response form;
    wherein the writing instrument is configured to mark a first response area of the response form using the first tip member thereby marking the first response area with the first fluid, to mark a second response area of the response form using the first tip member thereby marking the first response area with the first fluid, and to mark the first response area of the response form using the second tip member thereby marking the first response area with the second fluid so that the second fluid covers the first fluid; and
    wherein the response form that has been marked with the first and second fluids of the writing instrument is capable of being read using an optical apparatus such that a result of reading the first response area is different than a result of reading the second response area.

20. A writing instrument comprising:
    a housing having a main axis;
    a first reservoir located in the housing, the first reservoir for dispensing a first fluid having a first property of reflectivity;
    a first tip member in fluid connection with the first reservoir, the first tip member extending parallel to a main axis of the housing;
    a second reservoir located in the housing, the second reservoir for dispensing a second fluid that is capable of modifying the first property of reflectivity when covering the first fluid; and
    a second tip member in fluid connection with the second reservoir, the second tip member extending at an acute angle relative to the main axis of the housing.

* * * * *